United States Patent
Arnin

(10) Patent No.: US 7,947,063 B2
(45) Date of Patent: May 24, 2011

(54) POSTERIOR-MEDIAL FACET SUPPORT ASSEMBLY

(75) Inventor: Uri Arnin, Kiryat Tivon (IL)

(73) Assignee: Spine21 Ltd., Haifa (IL)

( * ) Notice: Subject to any disclaimer, the term of this patent is extended or adjusted under 35 U.S.C. 154(b) by 178 days.

(21) Appl. No.: 11/937,009

(22) Filed: Nov. 8, 2007

(65) Prior Publication Data

US 2009/0125064 A1    May 14, 2009

(51) Int. Cl.
  *A61B 17/70* (2006.01)
(52) U.S. Cl. ............ 606/247; 606/259; 606/261
(58) Field of Classification Search .......... 606/250, 606/261, 246–249, 264–279, 300–321; 623/17.11
  See application file for complete search history.

(56) References Cited

U.S. PATENT DOCUMENTS

| 2005/0131537 A1* | 6/2005 | Hoy et al. ............... 623/17.11 |
| 2006/0084991 A1* | 4/2006 | Borgstrom et al. ........... 606/61 |

* cited by examiner

*Primary Examiner* — Eduardo C Robert
*Assistant Examiner* — Christina Negrelli
(74) *Attorney, Agent, or Firm* — Dekel Patent Ltd; David Klein

(57) ABSTRACT

A facet support assembly including at least one rod including an upper portion rigidly fixed to a spinal fastener, and a lower portion configured to support an inferior articular process, wherein when the spinal fastener is secured to a pedicle of a lumbar vertebra, the lower portion of the at least one rod abuts against and supports the inferior articular process of the same lumbar vertebra.

11 Claims, 2 Drawing Sheets

POSTERIOR-MEDIAL FACET SUPPORT ASSEMBLY

FIELD OF THE INVENTION

The present invention is generally related to apparatus and methods for spinal prostheses or implants, and particularly to a posterior-medial facet support assembly.

BACKGROUND OF THE INVENTION

Through the course of life, disease or injury, the spinal canal, the laminae, or facets of one or more vertebral bodies can degenerate or become damaged, such that the spinal cord and/or nerve roots become compressed. This can result in an undesired anatomy, loss of mobility, and pain or discomfort. For example, spinal stenosis, as well as spondylosis, spondylolisthesis, osteoarthritis and other degenerative phenomena may cause back and leg pain. Such phenomena may be caused by a narrowing of the spinal canal by a variety of causes that result in the pinching of the spinal cord and/or nerves in the spine.

Decompression and fusion of two or more adjacent vertebrae are common options for treating these problems. However, it is known that fusion tends to cause the degeneration to migrate to adjacent vertebral levels. Thus, non-fusion solutions are desirable for the treatment of the above mentioned degenerative problems.

SUMMARY OF THE INVENTION

The present invention seeks to provide an improved posterior-medial facet support assembly, as described in more detail further below. The present invention provides a posterior and medial support for the native facets after a bony decompression procedure. The present invention seeks to provide a minimal invasive, motion preserving, novel spinal implant. The assembly is mainly advantageous for the posterior portion of the spine, but is not limited to this specific area.

One of the chief functions of the native facets is to stabilize the spinal segment and prevent excessive motion in the different directions. Each vertebra has two bilateral superior processes that create two bilateral joints with the two bilateral inferior processes of the vertebra above and two bilateral inferior processes that create two joints with the bilateral superior processes of the vertebra bellow. The two bilateral inferior processes of each vertebra are supported by the lamina and the pars to have the proper mechanical strength.

After a decompression procedure, a significant amount of the facet's bony support may be removed and thus its ability to stabilize the spine is compromised. The present invention seeks to provide the needed support for the facets so that they can properly stabilize the segment even after a wide decompression.

There is thus provided in accordance with a non-limiting embodiment of the present invention a facet support assembly including at least one rod including an upper portion rigidly fixed to a spinal fastener, and a lower portion configured to support an inferior articular process, wherein when the spinal fastener is secured to a pedicle of a lumbar vertebra, the lower portion of the at least one rod abuts against and supports the inferior articular process of the same lumbar vertebra.

In one embodiment, the spinal fastener includes a head of a polyaxial screw.

In a preferred embodiment, the facet support assembly includes left and right rods whose upper portions are rigidly fixed to left and right spinal fasteners, respectively, wherein when the left and right spinal fasteners are respectively secured to left and right pedicles of a lumbar vertebra, the lower portions of the left and right rods abut against and support the left and right inferior articular processes of the same lumbar vertebra. In one embodiment, the upper portion of the at least one rod is curved. In another embodiment, a cross bar connects the left and right facet support assemblies.

In yet another embodiment, a cross bar is attached to the left and right spinal fasteners, and the upper portions of the left and right rods are rigidly secured to the cross bar by mechanical fasteners.

There is also provided in accordance with a non-limiting embodiment of the present invention a facet support assembly including at least one rod including an upper portion rigidly fixed to a spinal fastener, and a lower portion formed with a depression, and a lower supporting element including a head shaped to mate with the depression, wherein when the spinal fastener is secured to a pedicle of a lumbar vertebra, the lower supporting element is positioned to support and abut against an inferior articular process of the same lumbar vertebra, and the head of the lower supporting element abuts against the depression of the lower portion of the at least one rod.

In one embodiment, a mechanical fastener secures the head of the lower supporting element with the depression of the lower portion of the at least one rod. In one embodiment, the depression is concave and generally spherical and the head is convex and generally spherical.

In another embodiment, left and right rods abut against left and right lower supporting elements.

In yet another embodiment, the spinal fastener includes a cross bar attached to left and right polyaxial screws, and the upper portions of the left and right rods are rigidly secured to the cross bar by mechanical fasteners.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1A:
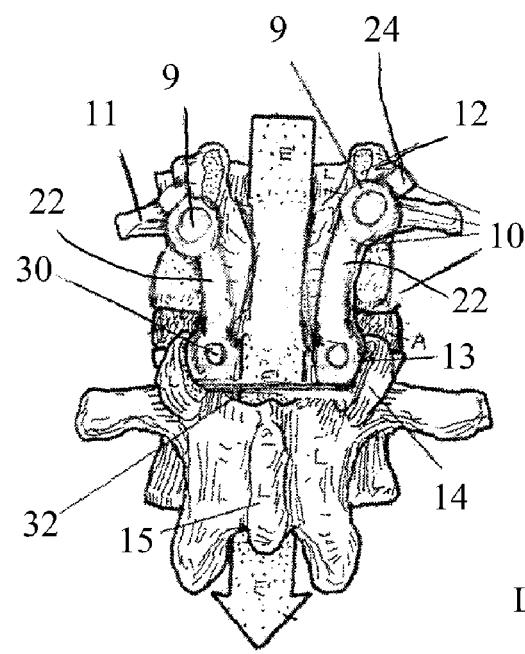
FIGS. 1A and 1B are simplified posterior-view and lateral-view illustrations of a posterior-medial facet support assembly, respectively, constructed and operative in accordance with an embodiment of the present invention.
Figure 1B:
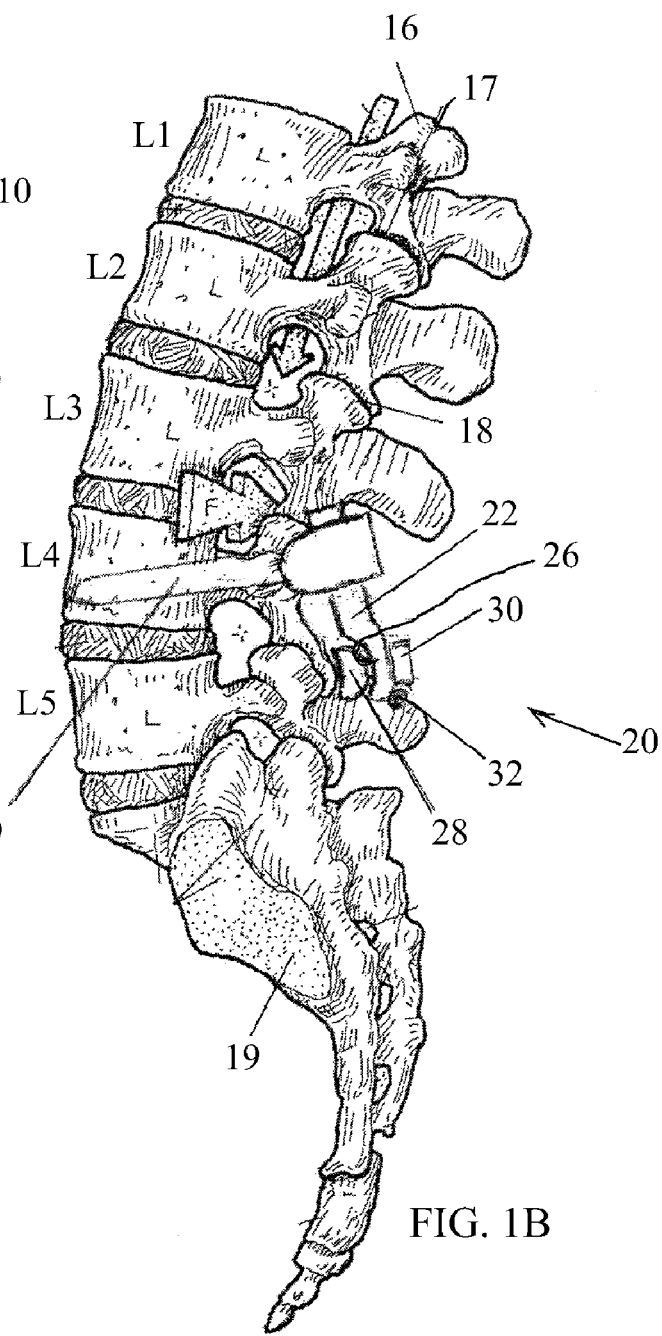

FIG. 1A illustrates the area of two adjacent lumbar vertebrae, showing the body 10 of the vertebra, the transverse process 11, superior articular process 12, and inferior articular process 13 of the superior vertebra, and the superior articular process 14 and spinous process 15 of the inferior vertebra. FIG. 1B illustrates the area of the L1-L5 vertebrae, showing the L1 superior articular process 16, L1 inferior articular process 17, a facet joint 18 between L2 and L3, and the auricular surface 19 for the iliac bone.

As seen in FIG. 1B, a laminectomy decompression has been performed on L4, wherein the spinous process and the lamina have been removed. Two polyaxial pedicle screws 9 have been screwed into the pedicles of L4.

In accordance with an embodiment of the present invention, as illustrated in FIGS. 1A-1B, a posterior-medial facet support assembly 20 is provided for helping support the facets. The facet support assembly 20 includes at least one rod 22, whose upper portion 24 is rigidly fixed to the head of the polyaxial screw 9. It is noted that the term "rod" throughout the specification and claims is not limited to a round slender element, but also encompasses any slender element of any geometrical shape, such as but not limited to, a bar, wire, etc. of square, round, elliptical, hexagonal and other shapes.

Although for certain situations, it is possible to carry out the invention with just one rod 22 on either the left or right side pedicle, for most situations, two rods 22, one on the left pedicle and the other on the right pedicle are employed. The upper portion 24 of rod 22 may be curved or bent to suit the geometry of the inferior articulating process and nearby structure.

The lower portion of rod 22 by itself may be used to support the inferior articular process 13, by abutting against the inferior articular process 13. Note that the upper portion of rod 22 is fixed (e.g., by means of polyaxial screw 9) to the pedicle of the same vertebra as the inferior articular process 13.

In accordance with an embodiment of the present invention, the lower portion of rod 22 is not used by itself to support the inferior articular process 13. Instead, the lower portion of rod 22 is formed with a concave, generally spherical depression 26, which may be secured to a lower supporting element 28 with a mechanical fastener 30 (e.g., screw). The head of the lower supporting element 28 is convex and generally spherical to match (mate with) and abut against the generally spherical depression 26. (Other shapes than convex and concave may also be used to carry out the invention.) Lower supporting element 28 is positioned to support and abut against the inferior articular process 13 of the same lumbar vertebra. Optionally, a cross bar 32 may be used to connect the left and right sides of the facet support assembly 20.

The facet support assembly 20 is highly adaptable to the native morphology and geometry of the patient. The polyaxial screw head of polyaxial screw 9 may be oriented to fix rod 22 at the required rotational and translational position. The interface of lower supporting element 28 with the depression 26 of the lower portion of rod 22 may also be adjusted to any spatial orientation before fixing with mechanical fastener 30 and optionally cross bar 32.

Figure 2A:
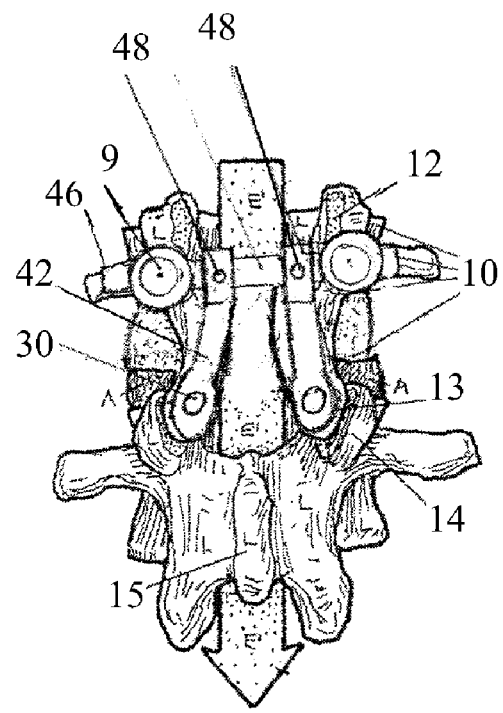
FIGS. 2A and 2B are simplified posterior-view and lateral-view illustrations of a posterior-medial facet support assembly, respectively, constructed and operative in accordance with another embodiment of the present invention.
Figure 2B:
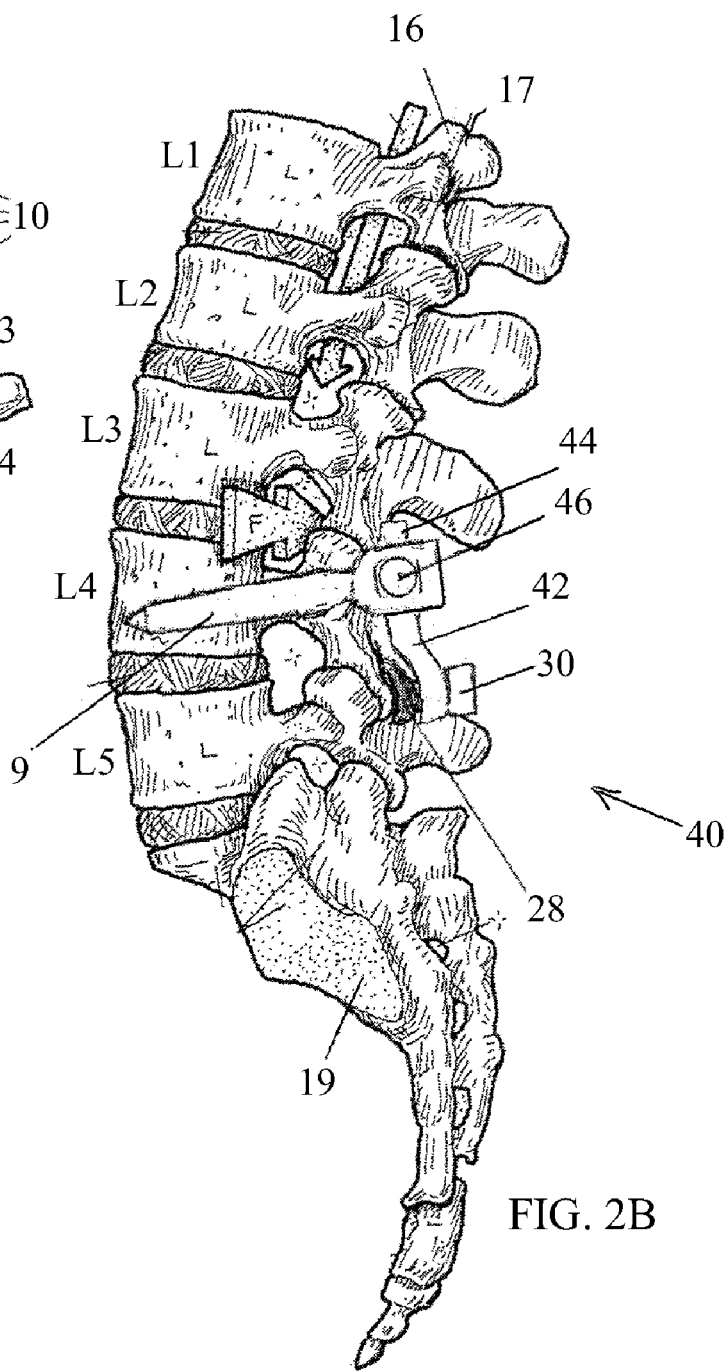

Reference is now made to FIGS. 2A and 2B, which illustrate a posterior-medial facet support assembly 40, constructed and operative in accordance with another embodiment of the present invention. The facet support assembly 40 is constructed similarly to the facet support assembly 20, and like elements are designated by like numerals.

The facet support assembly 40 differs from facet support assembly 20 in that rods 42 of facet support assembly 40 are not fixed at their upper portions 44 to the pedicle screws 9. Instead, a cross bar 46 is attached to and connects the two pedicle screws 9. Cross bar 46 is held rigidly by the heads of the polyaxial screws 9. The upper portions 44 of rods 42 are rigidly secured to cross bar 46 by mechanical fasteners (e.g., set screws) 48. Because of the different attachment points, the rods 42 are shaped somewhat differently from rods 22 of facet support assembly 20.

The facet support assembly 40 is also highly adaptable to the native morphology and geometry of the patient. The polyaxial screw head of polyaxial screw 9 may be oriented to fix cross bar 46, and subsequently rod or rods 42 fixed to cross bar 46 with mechanical fastener 48, at the required rotational and translational position. The interface of lower supporting element 28 with the depression 26 of the lower portion of rod 42 may also be adjusted to any spatial orientation before fixing with mechanical fastener 30 (and optionally a lower cross bar 32).

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A facet support assembly comprising:
at least one rod comprising an upper portion rigidly fixed to a spinal fastener, and a non-articulating lower portion configured to support an inferior articular process, wherein when said spinal fastener is secured to a pedicle of a lumbar vertebra, said lower portion of said at least one rod abuts against and supports the inferior articular process of said same lumbar vertebra, wherein said at least one rod comprises left and right rods whose upper portions are rigidly fixed to left and right spinal fasteners, respectively, wherein when said left and right spinal fasteners are respectively secured to left and right pedicles of a lumbar vertebra, the lower portions of said left and right rods abut against and support the left and right inferior articular processes of said same lumbar vertebra.

2. The facet support assembly according to claim 1, wherein said spinal fastener comprises a head of a polyaxial screw.

3. The facet support assembly according to claim 1, wherein said upper portion of said at least one rod is curved.

4. The facet support assembly according to claim 1, further comprising a cross bar that connects said left and right facet support assemblies.

5. The facet support assembly according to claim 1, wherein a cross bar is attached to said left and right spinal fasteners, and the upper portions of said left and right rods are rigidly secured to said cross bar by mechanical fasteners.

6. A facet support assembly comprising:
at least one rod comprising an upper portion rigidly fixed from a posterior direction to a spinal fastener, and a lower portion formed with an anterior depression; and
a lower supporting element comprising a head shaped to mate with said depression, wherein when said spinal fastener is secured to a pedicle of a lumbar vertebra, said lower supporting element is positioned to support and abut against an inferior articular process of said same lumbar vertebra, and said head of said lower supporting element abuts anteriorly against said anterior depression of the lower portion of said at least one rod.

7. The facet support assembly according to claim 6, further comprising a mechanical fastener that secures said head of said lower supporting element with said depression of the lower portion of said at least one rod.

8. The facet support assembly according to claim 7, further comprising a lower cross bar adjacent said mechanical fastener.

9. The facet support assembly according to claim 6, wherein said depression is concave and generally spherical and said head is convex and generally spherical.

10. The facet support assembly according to claim 6, comprising left and right rods that abut against left and right lower supporting elements.

11. The facet support assembly according to claim 10, wherein said spinal fastener comprises a cross bar attached to left and right polyaxial screws, and the upper portions of said left and right rods are rigidly secured to said cross bar by mechanical fasteners.

* * * * *